United States Patent [19]
Peeno

[11] Patent Number: 5,964,734
[45] Date of Patent: Oct. 12, 1999

[54] SELF ADHESIVE CATHETER TUBE

[76] Inventor: Barbara M. Peeno, 5652 31st Ave. N., St. Petersburg, Fla. 33710

[21] Appl. No.: 08/987,417

[22] Filed: Dec. 9, 1997

[51] Int. Cl.[6] ................................................ A61M 5/32
[52] U.S. Cl. .................. 604/180; 604/174; 128/DIG. 6
[58] Field of Search .................... 604/174, 180, 604/177, 179; 128/DIG. 26, 133, DIG. 6; 602/54, 57

[56] References Cited

U.S. PATENT DOCUMENTS

| | | | |
|---|---|---|---|
| 3,194,235 | 7/1965 | Cooke | 128/132 |
| 3,288,136 | 11/1966 | Lund | 128/133 |
| 3,885,560 | 5/1975 | Baldwin | 128/214 R |
| 4,324,236 | 4/1982 | Gordon et al. | 128/214 R |
| 4,449,975 | 5/1984 | Perry . | |
| 4,690,675 | 9/1987 | Katz | 604/177 |
| 4,698,057 | 10/1987 | Joishy | 604/176 |
| 4,743,232 | 5/1988 | Kruger | 604/180 |
| 4,822,342 | 4/1989 | Brawner . | |
| 4,874,380 | 10/1989 | Hesketh . | |
| 4,976,698 | 12/1990 | Stokley . | |
| 5,037,397 | 8/1991 | Kalt et al. | 604/174 |
| 5,112,313 | 5/1992 | Sallee | 604/180 |
| 5,135,506 | 8/1992 | Gentelia et al. . | |
| 5,167,639 | 12/1992 | Hollands et al. . | |
| 5,219,336 | 6/1993 | Wilk . | |
| 5,221,265 | 6/1993 | List . | |
| 5,236,421 | 8/1993 | Becher . | |
| 5,282,791 | 2/1994 | Lipton et al. . | |
| 5,306,256 | 4/1994 | Jose . | |
| 5,496,283 | 3/1996 | Alexander . | |
| 5,704,917 | 1/1998 | Utterberg | 604/180 |

Primary Examiner—Corrine McDermott
Assistant Examiner—Cris L. Rodriguez
Attorney, Agent, or Firm—Kenneth L Tolar

[57] ABSTRACT

The present invention relates to a self-adhering catheter tube assembly including an elongated tubular member having a needle extending from one of two ends and an adhesive strip on the exterior surface thereof. An L-shaped tongue protrudes from the exterior surface of the tubular member for selectively engaging an L-shaped opening on a sleeve member. The transparent sleeve member surrounds the exterior of the tubular member and selectively covers the adhesive strip by coupling the L-shaped opening with the L-shaped tongue. Accordingly, the sleeve may be rotated and slid axially with respect to the tubular member to expose the adhesive strip. A removable protective layer covers the adhesive strip allowing the tubular member to be quickly and easily secured to a patient's skin. When the tubular member is removed from a patient, the sleeve may be slid back over the adhesive strip and locked into place by coupling the L-shaped tongue with the opening to prevent the tubular member from inadvertently adhering to a person's fingers, clothing or other surrounding objects.

5 Claims, 2 Drawing Sheets

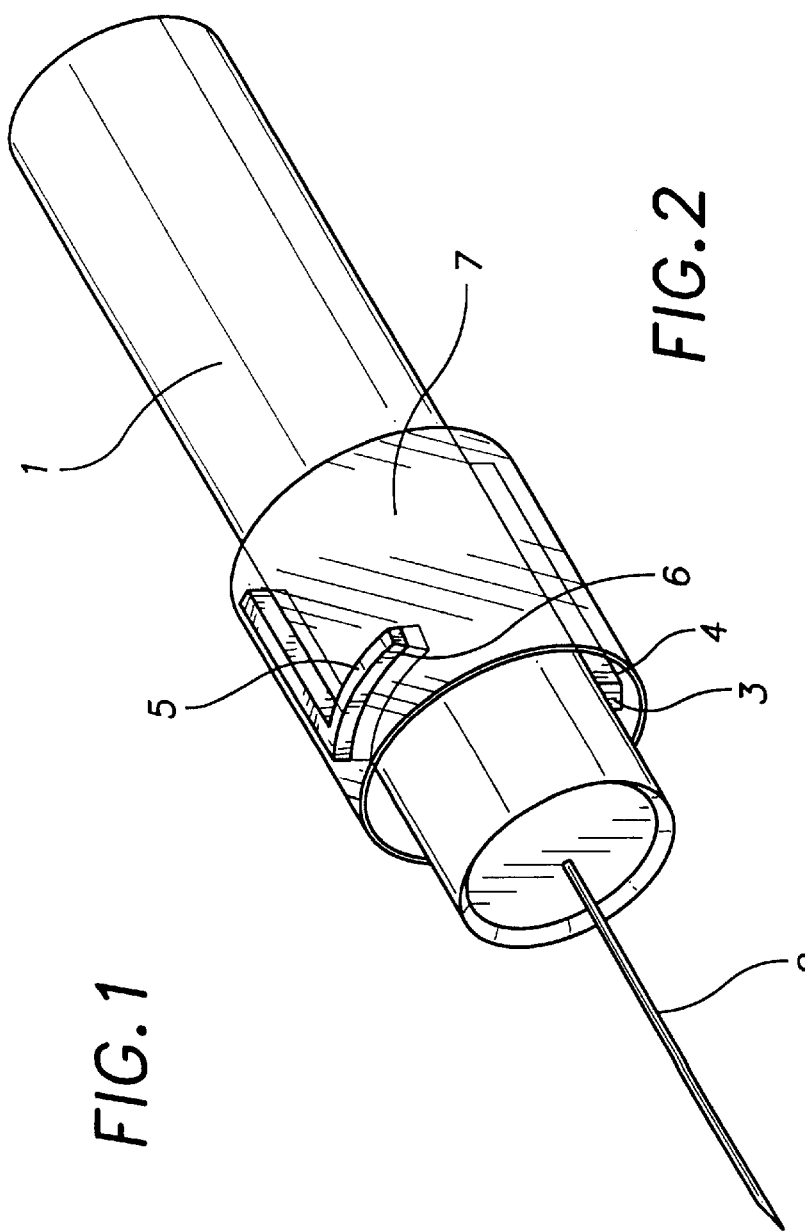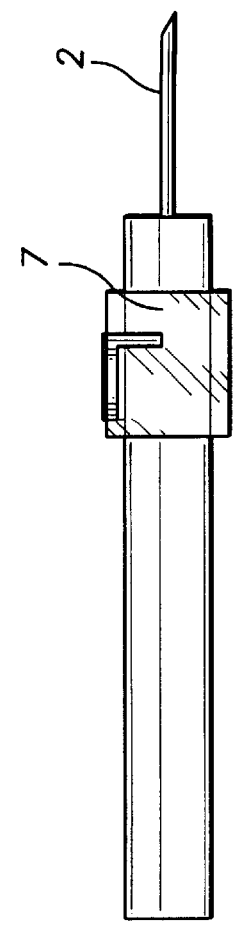

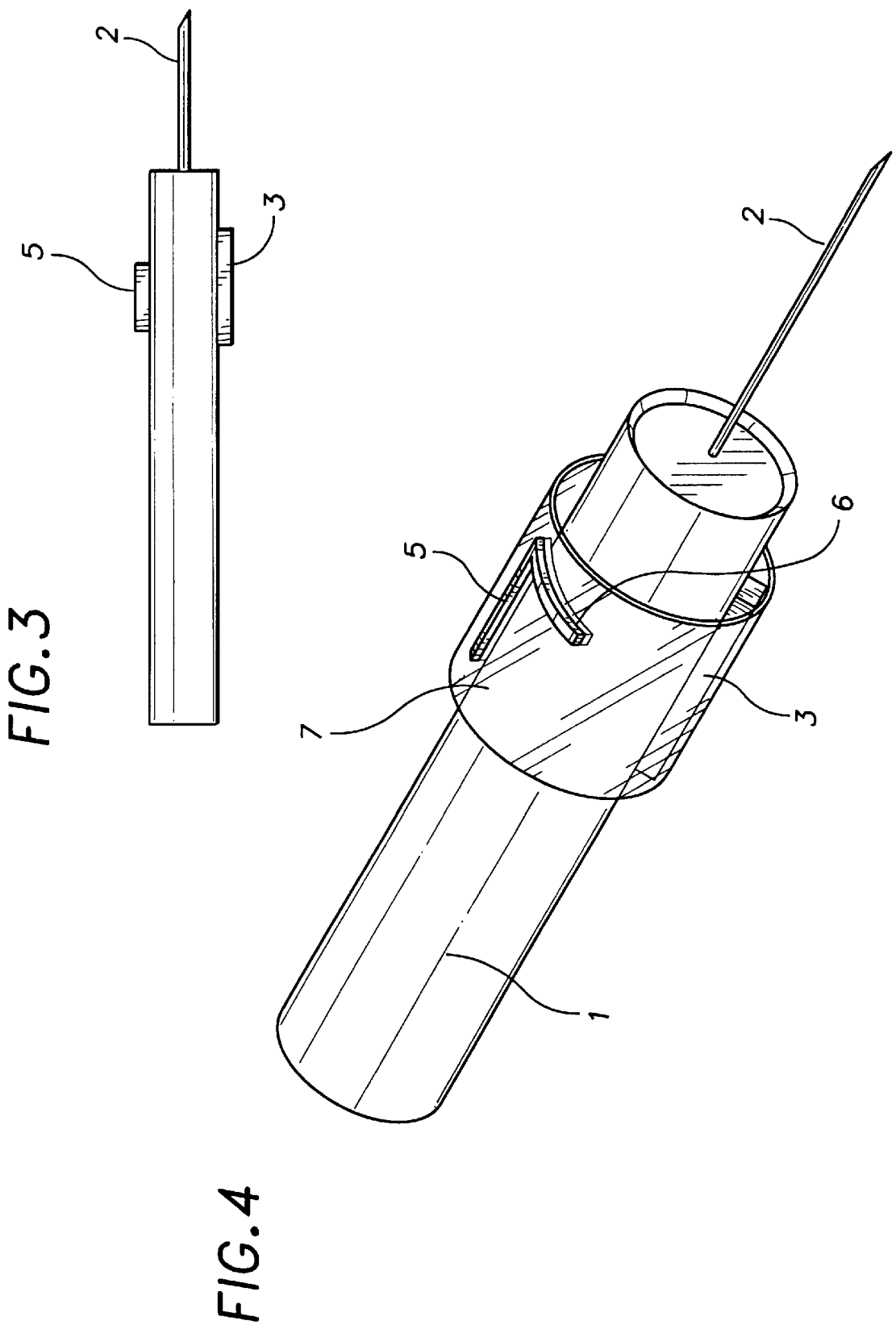

SELF ADHESIVE CATHETER TUBE

BACKGROUND OF THE INVENTION

The present invention relates to a catheter tube with an adhesive material on its exterior surface for attaching to a patient's skin. The adhesive material is selectively coverable with a concentric transparent sleeve releasably secured to the tube exterior.

DESCRIPTION OF THE PRIOR ART

Catheter tubes and the like are used in conjunction with needles and intravenous tubes for introducing fluids into a patient's body or removing fluids therefrom. Typically, these devices are secured to a patient's limb with tape, straps or other similar attachment means. In order to secure the device, however, a nurse or other health care worker must typically hold the catheter with one hand while attaching it with the other which is cumbersome and difficult. Alternatively, an assistant must hold the catheter while the health care worker secures it to the patient.

Numerous devices have been heretofore designed to temporarily secure a catheter or a similar device to a patient's limb so that it may be permanently attached thereto. Many of these devices include numerous interrelated components and are difficult to use and manufacture. Furthermore, these devices do not relate to a catheter tube having an integral attachment means as does the present invention. For example, U.S. Pat. No. 5,496,283 issued to Alexander relates to a circular pad having a clamp on one side for receiving an IV tube and adhesive material on the other side for attaching the device to the patient's skin. The device is designed to prevent the catheter from being dislodged if the tube is inadvertently pulled or displaced.

U.S. Pat. No. 5,135,506 issued to Gentelia relates to a cannula holding device comprising a pad having a V-shaped projection extending therefrom. The projection has an adhesive layer thereon for adhesively surrounding a cannula. The pad is then adhesively secured to the patient's skin.

U.S. Pat. No. 4,976,698 issued to Stokley relates to an IV catheter and tubing stabilization device comprising a base having an arcuate slot to receive and stabilize the catheter tubing and a cover removably attached to the base. The base is attached to a patient's limb using one or more flexible adhesive straps.

U.S. Pat. No. 4,874,380 issued to Hesketh relates to a catheter retaining device comprising a flange having a central hole with a post extending therefrom. An elongated tab extends from the post with a slot thereon for receiving the free end of the tab. The tab surrounds a catheter protruding through the hole and is then passed through the slot in order to grip the catheter. The device is mounted on an adhesive pad for securing to a patient.

U.S. Pat. No. 4,822,342 issued to Brawner relates to a prepared tape for securing IV needles, catheters and/or associated tubing comprising lengths of a base tape and an anchoring tape each having a pressure sensitive surface and a non-adherent backing. The anchoring tape's adhesive surface may be wrapped onto the device to be secured.

U.S. Pat. No. 4,449,975 issued to Perry relates to an intravenous anchor and wound shield using an adhesively attached base member and cooperating securing straps.

U.S. Pat. No. 5,282,791 issued to Lipton et al discloses a device for securing a catheter tube comprising a flat body portion with an adhesive layer for securing the body portion to a person's skin and a second adhesive layer for attaching the body portion to a catheter tube.

Although various catheter and IV tube securing devices exist in the prior art, none of these devices relate to a catheter tube having a small adhesive portion integral with its exterior surface. When preparing a patient for an IV, a blood transfusion or similar procedures, a health care worker must secure the catheter to the patient as quickly as possible since every second is critical and in some cases, a matter of life and death. The above described devices which use an adhesive substance or pad do not adequately solve the problems associated with quickly securing the catheter to a patient's limb. Because a separate pad or securing device is used, the securing device must first be adhesively attached to a patient's skin. The securing device must then be attached to the catheter or tubing in a multi-step, time consuming process. Accordingly, these devices often require as much time and effort as the more conventional methods of holding and taping the catheter. Furthermore, when catheters having an adhesive substance thereon are removed from a patient, they often adhere to surrounding objects such as a user's clothing or fingers causing aggravation, inconvenience and possible health risks.

The present invention overcomes these disadvantages by providing a catheter tube having an adhesive strip on its exterior surface for quickly attaching the tube to a patient's skin so that the tube may be temporarily secured thereto in a quick, one step process. The adhesive strip is selectively coverable using a transparent sleeve releasably secured to the tube exterior. Accordingly, when the catheter is removed from a patient, the sleeve may be quickly slid over the adhesive strip to prevent the catheter from inadvertently adhering to a person's clothing, fingers or other surrounding objects.

SUMMARY OF THE INVENTION

The present invention overcomes the above enumerated disadvantages of the prior art by providing a catheter tube assembly comprising an elongated tubular member having two ends with a needle extending from an end thereof. Projecting from the exterior surface of the tubular member is a strip with an adhesive substance on its exterior surface. The adhesive substance may be selectively exposed using a removable protective layer. Also disposed on the exterior surface of the tubular member is an L-shaped tongue. Surrounding the tubular member is a transparent sleeve having an L-shaped opening for selectively receiving the L-shaped tongue. Accordingly, the transparent sleeve is superimposed on the adhesive strip and is locked into place by inserting the L-shaped tongue into the L-shaped opening. To attach this device to a patient, a user rotates the sleeve to release it from the L-shaped tongue and slides the sleeve axially with respect to the tubular member to expose the adhesive strip. The protective layer is removed and the catheter may be temporarily secured to a person's skin. A nurse or other health care worker may then permanently secure the catheter thereto using any conventional means such as tape, bands, straps, etc. When the device is removed, the sleeve may be quickly slid over the adhesive strip and locked in place using the L-shaped tongue and opening mechanism to assure that the tubular member does not inadvertently adhere to a surrounding surface. It is therefore an object of the present invention to provide a catheter tube assembly having means for quickly securing the device to a patient's skin.

It is yet another object of the present invention to provide a catheter tube assembly in which the means for attaching the tube to a patient's skin may be quickly and conveniently covered to prevent the tube from inadvertently adhering to a person's clothing, fingers, etc. when the tube is removed therefrom.

It is yet another object of the present invention to provide a catheter tube assembly in which the adhesive covering means may be releasably coupled to the tube exterior. Other objects, features and advantages of the present invention will become readily apparent from the following detailed description of the preferred embodiment when considered with the attached drawings and the appended claims.

BRIEF DESCRIPTION OF THE DRAWINGS

FIG. 1 depicts the inventive device.

FIG. 2 depicts a second orientation of the inventive device.

FIG. 3 depicts the inventive device depicted in FIG. 2 with the sleeve removed therefrom.

FIG. 4 depicts the inventive device with the transparent sleeve thereon.

DESCRIPTION OF THE PREFERRED EMBODIMENT

Referring now to FIGS. 1 through 4, the present invention relates to a self adhering catheter tube assembly comprising an elongated tubular member 1 having an exterior surface and two ends. Projecting outwardly from an end thereof is a needle 2 for penetrating a patient's skin. Disposed on the exterior surface of the tubular member is an adhesive strip 3 for selectively attaching the tubular member 1 to a patient's skin. The strip 3 has a medical grade adhesive substance of the type generally known in the prior art on the exterior surface thereof. The adhesive substance may be selectively covered using a removable protective layer 4.

Projecting from the exterior surface of the tubular member 1 is an L-shaped tongue 5 for securing a sleeve 7 as will be described below. Surrounding the tubular member 1 is a transparent cylindrical sleeve 7 having an L-shaped opening 6 thereon dimensioned to tightly receive the L-shaped tongue 5 on the exterior surface of the tubular member 1.

When the device is not in use, the sleeve 7 covers the adhesive strip 3 and is locked onto the tubular member with the L-shaped tongue 5 inserted into the sleeve opening 6. When attaching the device to a patient's skin, the sleeve 7 is rotated to separate the sleeve 7 from the L-shaped tongue and the sleeve 7 is slid axially along the tubular member 1 to expose the adhesive strip 3. The protective layer 4 is then removed from the adhesive strip 3 and the catheter tube assembly may be quickly and easily attached to a patient's skin allowing a medical care professional to use both hands while permanently securing the device.

When removing the device from the patient, a user may quickly slide the transparent sleeve 7 back over the adhesive strip 3 and rotate it until the tongue 5 protrudes through the sleeve opening 6 to secure the sleeve 7 to the tubular member. Accordingly, the catheter tube assembly may be quickly discarded without the possibility of it inadvertently adhering to a person's clothing, fingers or other surrounding objects. The size, shape and materials of construction of the related components may be varied to suit a particular application. In addition, it is preferred that the sleeve is constructed with a lightweight, transparent plastic or similar material. However, the sleeve may be opaque as well.

Although there has been shown and described the preferred embodiment of the present invention it will be readily apparent to those skilled in the art that modifications may be made thereto which do not exceed the scope of the appended claims. Therefore, the scope of the invention is to only be limited by the following claims.

What is claimed is:

1. A self-adhering catheter tube assembly which may be quickly and easily secured to a patient's body comprising:

an elongated tubular member having an exterior surface and two opposing ends;

a needle extending from one of said ends;

a strip on the exterior surface of said tubular member, said strip having an exterior surface with an adhesive substance thereon;

a covering means surrounding said tubular member selectively superimposable on said adhesive strip;

a cylindrical sleeve surrounding said tubular member and axially translatable thereon, said sleeve having an opening;

a tongue projecting from the exterior surface of said tubular member, said tongue dimensioned to be tightly received within said opening to releasably secure said sleeve to the exterior surface of said tubular member thereby covering said adhesive strip.

2. A catheter tube assembly according to claim 1 wherein said adhesive strip has a removable protective layer on the exterior surface thereof for selectively exposing said adhesive substance.

3. A catheter tube assembly according to claim 1 wherein said sleeve is transparent.

4. A catheter tube assembly according to claim 1 wherein said adhesive substance is a medical grade adhesive.

5. A catheter tube assembly according to claim 1 wherein said opening and said tongue are substantially L-shaped.

* * * * *